(12) United States Patent
Mitchell

(10) Patent No.: US 8,997,761 B1
(45) Date of Patent: Apr. 7, 2015

(54) MINI-TOOTHBRUSH WITH FLOSSER

(71) Applicant: Dean MacCauther Mitchell, Panama City, FL (US)

(72) Inventor: Dean MacCauther Mitchell, Panama City, FL (US)

( * ) Notice: Subject to any disclaimer, the term of this patent is extended or adjusted under 35 U.S.C. 154(b) by 0 days.

(21) Appl. No.: 14/170,182

(22) Filed: Jan. 31, 2014

(51) Int. Cl.
| | |
|---|---|
| *A45D 44/18* | (2006.01) |
| *A61C 15/00* | (2006.01) |
| *B65D 83/10* | (2006.01) |
| *A46B 9/04* | (2006.01) |
| *A45B 15/00* | (2006.01) |
| *A46B 15/00* | (2006.01) |
| *A61C 15/04* | (2006.01) |

(52) U.S. Cl.
CPC ......... *A46B 15/0071* (2013.01); *A46B 15/0073* (2013.01); *A61C 15/046* (2013.01)

(58) Field of Classification Search
CPC ............... A46B 5/026; A46B 15/0055; A46B 15/0071; A46B 15/0073; A46B 9/045; A46B 5/0012; A46B 5/0008; A46B 2200/1066; A61C 15/041; A61C 15/046
USPC ......... 132/309, 286, 310, 311, 313, 308, 321, 132/323, 329; 15/21.1, 111, 167.1, 167.2; 206/361, 362, 362.1, 362.2, 362.3, 206/368, 369, 63.5, 209.1; D4/104–108, D4/116, 118; D28/65–68
See application file for complete search history.

(56) References Cited

U.S. PATENT DOCUMENTS

| | | | | |
|---|---|---|---|---|
| 1,125,532 | A * | 1/1915 | Himmel | 15/117 |
| 1,958,505 | A * | 5/1934 | Aki | 132/309 |
| 2,233,936 | A * | 3/1941 | Campbell | 132/325 |
| D130,437 | S * | 11/1941 | Patterson | D4/106 |
| 4,588,089 | A * | 5/1986 | Yanz et al. | 206/581 |
| 5,181,531 | A * | 1/1993 | Escoto et al. | 132/308 |
| 5,184,719 | A * | 2/1993 | Gordon | 206/209.1 |
| 5,228,466 | A * | 7/1993 | Klinkhammer | 132/308 |
| 5,915,868 | A * | 6/1999 | Frazell | 401/132 |
| 6,092,536 | A * | 7/2000 | Owens | 132/325 |
| 6,119,296 | A * | 9/2000 | Noe et al. | 15/104.94 |
| 6,135,274 | A * | 10/2000 | James | 206/209.1 |
| 6,397,860 | B1 * | 6/2002 | Hill, II | 132/309 |
| 7,073,225 | B1 * | 7/2006 | Ford | 15/167.2 |
| 7,124,894 | B1 * | 10/2006 | Dobos | 206/581 |
| D599,557 | S * | 9/2009 | Crossman | D4/108 |
| D628,807 | S * | 12/2010 | Vazquez | D4/106 |
| 7,901,153 | B1 * | 3/2011 | Strider | 401/272 |
| D691,377 | S * | 10/2013 | Zarrabi et al. | D4/108 |
| 8,714,165 | B2 * | 5/2014 | Thomas | 132/309 |
| 2005/0211262 | A1 * | 9/2005 | Raab | 132/309 |
| 2010/0236006 | A1 * | 9/2010 | Deng | 15/167.2 |
| 2013/0220363 | A1 * | 8/2013 | Zarrabi et al. | 132/309 |

* cited by examiner

*Primary Examiner* — Vanitha Elgart

(57) ABSTRACT

A disposable mini-toothbrush comprises a brush and flosser head positioned at a first and second end of a handle portion. The brush head is comprised of a plurality of bristles that extend in opposite directions from a bristle supporting element. The plurality of bristles which extend in opposite directions facilitate cleaning of the upper and lower teeth without having to readjust grip by a user. The mini-toothbrush also comprises a first and second flat grip element to facilitate manipulation of the brush and flosser head while using only a thumb and at least one finger by the user. In its preferred embodiment, the plurality of bristles will be coated with dentifrice for cleaning is of the user's teeth and gums. A thin plastic cover surrounds and seals the toothbrush and provides a seal which maintains sterility during shipping and storage.

5 Claims, 1 Drawing Sheet

MINI-TOOTHBRUSH WITH FLOSSER

FIELD OF THE INVENTION

The present invention relates to a new disposable mini-toothbrush with a flossing device that is inexpensive, compact and easy to floss and brush.

BACKGROUND OF THE INVENTION

Generally, various disposable teeth cleaning devices for reducing the incidence of dental and periodontal disease are known, and typical prior art devices are shown in U.S. Pat. Nos. 3,165,776; 4,503,871; 4,522,524; 4,530,129; 4,588,089, 4,865,481, 4,966,176 and 5,184,719. Various arrangements have been proposed to combine a dual purpose toothbrush with a flossing device. Such device is discussed in the aforementioned U.S. Pat. No. 5,184,719. While there exist prior art toothbrushes with combining toothbrushes with a flossing device, there has yet to be provided a dual purpose toothbrush with a plurality of bristles which extend in opposite directions and connected to a flosser for cleaning ones teeth and gums. Also, a unique combination of flat grip elements and the oppositely disposed bristles enables a user to floss and brush one's teeth and gums while grasping with only thumb and at least one finger. Furthermore, the oppositely disposed bristles permits the user to more effectively cleaning the upper and lower teeth and gums without having to readjust the grip and while using only the thumb and at least one finger by the user. This unique design of the mini-toothbrush with flosser provides the user a more effective means for cleaning one's teeth and gums. The present invention achieves this.

SUMMARY OF THE INVENTION

It is the object of the present invention to provide an improve means for cleaning and flossing one's mouth, particularly the teeth, gums and inner mouth tissue.

The disposable mini-toothbrush includes a flosser head integrally attached to a handle portion. A first flat grip element is integrally connected to a first end of the handle permitting a user to place a thumb and at least one finger to provide enhanced grip for easy maneuverability of the brush head. The brush head includes a plurality of bristles which extend outward of at least two opposite directions to facilitate effective brushing of the user's upper and lower teeth and gums without the need for readjustment while gripping with a user's thumb and at least one finger. The handle also includes a second flat grip element between the floss portion and brush head to facilitate ergonomic gripping while enabling the user means for manipulation of the flosser head. The bristles of the brush head and the floss element in its preferred embodiment will be coated with dentifrice with the entire mini-toothbrush sealed using a thin plastic to prevent bacteria buildup during shipping and storage.

DETAILED DESCRIPTION OF THE DRAWINGS

Figure 1:
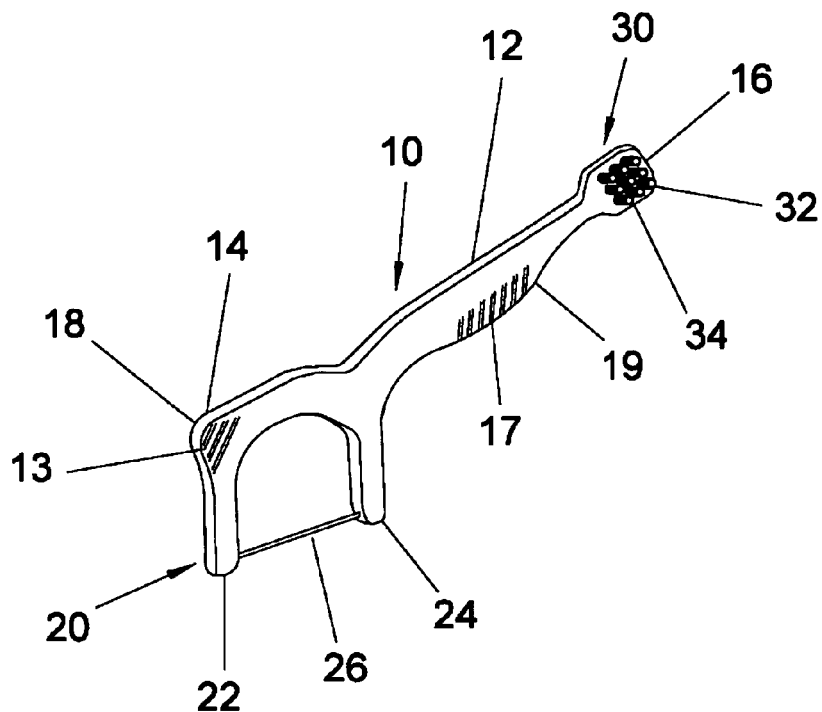
FIG. 1 is an external perspective view of the mini-toothbrush with flosser according to the present invention.
Figure 2:
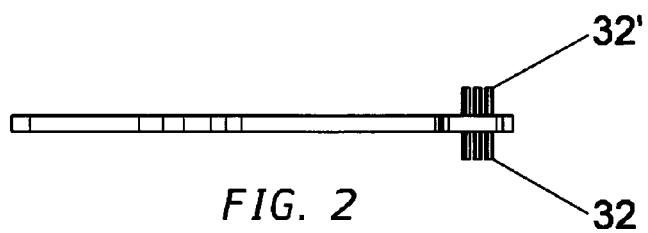
FIG. 2 is an external top plan view showing the plurality of bristles exposed in opposite directions.
Figure 3:
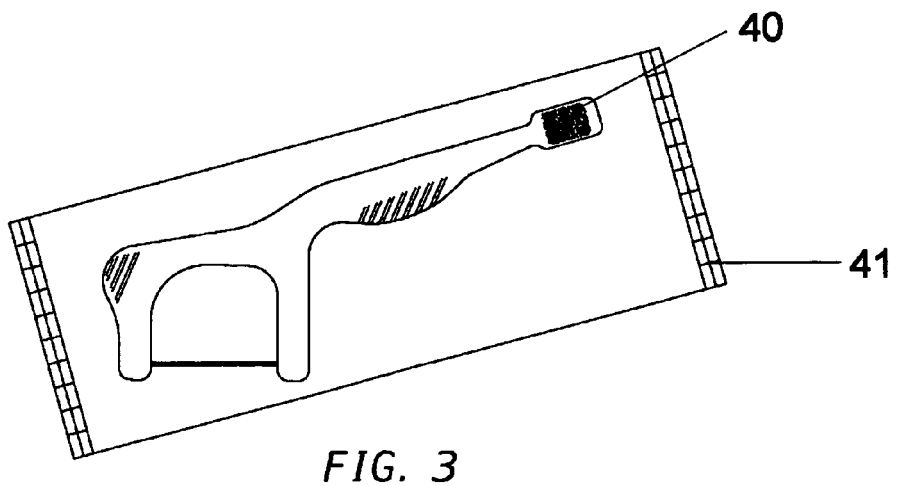
FIG. 3 is a side elevation view of the mini-toothbrush illustrating the vacuum sealed package and dentifrice coated bristles.

With reference to FIG. 1 and FIG. 2, the disposable mini-toothbrush according to the invention is generally designated by the numeral 10. The mini-toothbrush 10 comprises a handle portion 12 comprising a first and a second end 14,16. A first flat grip element 18 for manipulating a brush head 30 is integrally connected at the first end 14 of the handle portion 12. A second flat grip element 19 is integrally connected to the handle 12 between a flosser head 20 and the brush head 30 for manipulation of the flosser head 20 by a user. The flosser head 20 is comprised of a first and second fork element 22,24 wherein at least one floss element 26 is connected therebetween. A plurality of bristles 32,32' extend outward from at least two sides of a bristle supporting element 34 to facilitate cleaning of the upper and lower teeth without having to readjust the hold of the first flat grip element 18 while grasping with only a thumb and at least one finger by the user. The first and second flat grip elements 18,19 are comprised of a gripping surface 13,17 formed of voids and ridges or the like to facilitate ergonomic gripping between the thumb and at least one finger by the user. A dentifrice material 40 is shown in FIG. 3 coating the plurality of bristles 32,32', and the entire disposable mini-toothbrush 10 is vacuumed sealed in a suitable package 41.

Typically, the length of the handle portion 12 is approximately 2.5 to 3.0 inches long, varies in width approximately 0.25 to 0.5 inches, and 0.075 to 0.125 inches thick; brush head 30 is approximately 0.25 inches wide and 0.25 inches long; the distance between the fork elements 22,24, which determines the length of floss element 26, is approximately 0.5 to 0.75 inches wide; and the fork elements 22,24 themselves are approximately 0.5 to 0.75 inches long.

Those skilled in the art should appreciate that they can readily use the present invention as a basis for designing or modifying other processes and structure for carrying out the same purposes and/or achieving the same advantages of the embodiments introduced herein. Those skilled in the art should also realize that such equivalent constructions do not depart from the spirit and scope of the present invention.

What is claimed is:

1. A disposable toothbrush comprising: a handle portion with a first end and a second end, a flosser head integrally connected to said first end of said handle, said flosser head having first and second fork elements, and at least one floss element connected between said first and second fork elements, a brush head connected to said second end of said handle, said brush head having a bristle supporting element and having at least two oppositely disposed faces with a plurality of bristles extending from each of the faces, respectively, a first flat finger grip element integrally connected at the first end of the handle on the flosser head to facilitate brushing by a user, and a second flat finger grip element integrally connected to the handle between the flosser head and the brush head to facilitate flossing by the user.

2. The toothbrush of claim 1, further characterized in that said first flat finger grip element is formed of patterns using voids and ridges to facilitate grip by the user.

3. The toothbrush of claim 1, further characterized in that said second flat finger grip element is formed of patterns using voids and ridges to facilitate grip by the user.

4. The toothbrush of claim 1 in which said plurality of bristles being coated with a dentifrice paste.

5. The toothbrush of claim 4, in which a sealed cover is used to maintain said dentifrice paste and inhibiting bacteria buildup during storage and packaging.

* * * * *